(12) United States Patent
Schwartz et al.

(10) Patent No.: US 10,188,319 B2
(45) Date of Patent: Jan. 29, 2019

(54) METHOD OF PRODUCING A FOOT ORTHOTIC THROUGH 3D PRINTING USING FOOT PRESSURE MEASUREMENTS AND MATERIAL HARDNESS AND/OR STRUCTURE TO UNLOAD FOOT PRESSURE

(71) Applicant: AETREX WORLDWIDE, INC., Teaneck, NJ (US)

(72) Inventors: Laurence Schwartz, Teaneck, NJ (US); Evan Schwartz, Teaneck, NJ (US)

(73) Assignee: AETREX WORLDWIDE, INC., Teaneck, NJ (US)

( * ) Notice: Subject to any disclaimer, the term of this patent is extended or adjusted under 35 U.S.C. 154(b) by 0 days.

(21) Appl. No.: 15/896,999

(22) Filed: Feb. 14, 2018

(65) Prior Publication Data

US 2018/0228401 A1 Aug. 16, 2018

Related U.S. Application Data

(60) Provisional application No. 62/458,946, filed on Feb. 14, 2017.

(51) Int. Cl.
| | |
|---|---|
| *G06F 11/00* | (2006.01) |
| *A61B 5/103* | (2006.01) |
| *A43D 1/02* | (2006.01) |
| *A43B 7/14* | (2006.01) |
| *A43B 17/00* | (2006.01) |

(Continued)

(52) U.S. Cl.
CPC ............ *A61B 5/1038* (2013.01); *A43B 7/141* (2013.01); *A43B 17/003* (2013.01); *A43D 1/02* (2013.01); *A61B 2562/0247* (2013.01); *B33Y 10/00* (2014.12); *B33Y 30/00* (2014.12)

(58) Field of Classification Search
CPC .......... A43B 17/02; B33Y 10/00; B33Y 80/00
USPC ................................ 702/139, 140, 182–185
See application file for complete search history.

(56) References Cited

U.S. PATENT DOCUMENTS

| | | |
|---|---|---|
| 2007/0282562 A1 | 12/2007 | Schwartz et al. |
| 2012/0023776 A1 | 2/2012 | Skaja et al. |
| 2016/0235158 A1 | 8/2016 | DesJardine et al. |

(Continued)

OTHER PUBLICATIONS

International Search Report and Written Opinion for International Application No. PCT/US2018/018237 dated May 7, 2018, 8 pages.

*Primary Examiner* — Edward Raymond
(74) *Attorney, Agent, or Firm* — Lowenstein Sandler LLP

(57) ABSTRACT

A method and apparatus for generating a custom made orthotic or insole for footwear. Information relating to the pressure applied by the sole of a person's foot is used to custom produce an orthotic or insole for the person by using softer material or different structural components, selectively located at pressure points of a particular individual, to unload pressure on the foot at those points. Pressure readings taken for the foot of an individual identify pressure points for that foot. The pressure points are quantified and the foot is "mapped" in a grid format on a pressure map. Once mapped, structural components corresponding to a particular pressure value are positioned in the orthotic based on the mapping. The compression cells are created via 3D printing methods based on an individual's pressure readings and results from an electronic pressure plate utilizing pressure response sensors.

14 Claims, 20 Drawing Sheets

(51) Int. Cl.
 *B33Y 30/00* (2015.01)
 *B33Y 10/00* (2015.01)

(56) References Cited

U.S. PATENT DOCUMENTS

2016/0331071 A1    11/2016  Kane et al.
2016/0374431 A1*   12/2016  Tow .................... A43B 17/003
                                                36/43

* cited by examiner

METHOD OF PRODUCING A FOOT ORTHOTIC THROUGH 3D PRINTING USING FOOT PRESSURE MEASUREMENTS AND MATERIAL HARDNESS AND/OR STRUCTURE TO UNLOAD FOOT PRESSURE

CROSS-REFERENCE TO RELATED APPLICATIONS

This application is based on, and claims priority to, U.S. Provisional Application No. 62/458,946, filed on Feb. 14, 2017, the entire contents of which being fully incorporated herein by reference.

BACKGROUND OF THE INVENTION

Field of the Invention

The present invention relates to pedorthics for preventing and relieving foot problems and has particular applicability to orthotics custom made for an individual.

Description of the Related Art

Foot problems and the corresponding costs associated with foot care cost millions of dollars. In cases where the foot problem is debilitating for particular activities, a number of hours of work time can be lost. Foot problems can arise from medical conditions, work conditions requiring standing or walking, athletic activities, and the like. Thus, foot problems can develop from medical conditions, work activity or leisure activity.

Pedorthics is the art concerned with the design, manufacture, fit, and modification of footwear, foot orthotics, and foot appliances as prescribed to help relieve painful or disabling conditions of the foot. For those who practice any level of pedorthics, the goal is to provide protection and comfort to the consumer/patient. One of the primary ways of achieving this has been to reduce pressure at the greatest areas of impact. This has historically been accomplished with orthotics and/or external modifications to footwear.

One conventional method for providing protection and comfort to a consumer or patient is to use orthotics or insoles inserted into footwear to cushion the sole of the foot. There have also been products that reduce pressure by modifying a removable orthotic or insole that fits inside a shoe by removing selected pieces of the orthotic or insole.

There are generally two ways that orthotics are made in the prior art. In a first method, a cast of the foot is made to essentially provide a "template" for the eventual orthotic. According to this method, a hard thermoplastic material often is heated to soften it and then the softened thermoplastic material is molded to the cast of the foot so that the thermoplastic material takes the shape of the mold (and thus of the foot), and then it is cooled so that it becomes hard again. In a second method a mold is created from the cast of the foot and well-known injection molding techniques are used, typically whereby heated thermoplastic or thermosetting polymers are forced into the mold cavity where it cools and hardens to the configuration of the cavity.

More recently, 3D printing technology has been used essentially to custom produce the orthotics or insoles without the need to go through the processing steps described above to create the mold, heat the thermoplastic material, and then form it on or inject it into the mold. Instead, data defining the shape of the orthotic is input to the 3D printer to create the finished product in the same manner that any 3D-printed product is made. However, unlike the present invention, the end product in the prior art remains essentially the same as the end product created by the process for heat forming thermoplastics described in the prior art to produce a hard insert shaped to the foot of the user Commonly-assigned U.S. Pat. No. 7,493,230 discloses a method and apparatus for generating an orthotic or insole for footwear using information relating to pressure applied by the sole of a foot, which information is correlated to removable pieces of the orthotic or insole. Embodiments include a method and apparatus for generating an orthotic or insole for footwear, including receiving data from a pressure plate corresponding to a pressure map of the sole of a foot; determining regions of high relative pressure exceeding a predetermined relative pressure level within the pressure map; and associating data related to the regions of high relative pressure to an orthotic or insole including removable orthotic or insole pieces corresponding to the pressure map. In some embodiments a report is generated of the associated data related to the regions of high relative pressure. In a further embodiment the report provides information relating to the removable pieces of the orthotic or insole associated with the regions of high relative pressure.

While the above-described products and methods result in a reduced foot pressure, it would be desirable to have a method and system by which 3D-printing technology could be used to extract pressure information from the pressure map of the prior art and selectively vary the structure and/or material hardness at selected areas of a custom made orthotic or insole to custom make orthotic shoes or orthotics or insoles for individuals.

SUMMARY OF THE INVENTION

An advantage of the present invention is a method and apparatus for generating a custom made orthotic or insole for footwear. The inventive method and apparatus use information relating to the pressure applied by the sole of a person's foot to custom produce an orthotic or insole for the person by using different structural components, selectively located at pressure points of a particular individual, to unload pressure on the foot at those points. In a basic configuration the structural components can comprise, for example, individual compression cells having a generally-compressible lattice structure, that is, having an interlaced structure of compressible material configured in a regular repeated three-dimensional arrangement, as illustrated more fully in the accompanying drawings. Pressure readings taken for the foot of an individual identify pressure points for that foot. In a preferred embodiment the pressure points are quantified and the foot is "mapped" in a grid format on a pressure map. Once mapped, structural components corresponding to a particular pressure value are positioned in the orthotic based on the mapping. In a preferred embodiment the compression cells are created via 3D printing methods based on an individual's pressure readings and results from an electronic pressure plate utilizing pressure response sensors. A goal of invention is to unload foot pressure in high pressure areas of the foot by adjusting the orthotic material hardness, softness, and/or structure of the orthotic.

DETAILED DESCRIPTION

Figure 1:
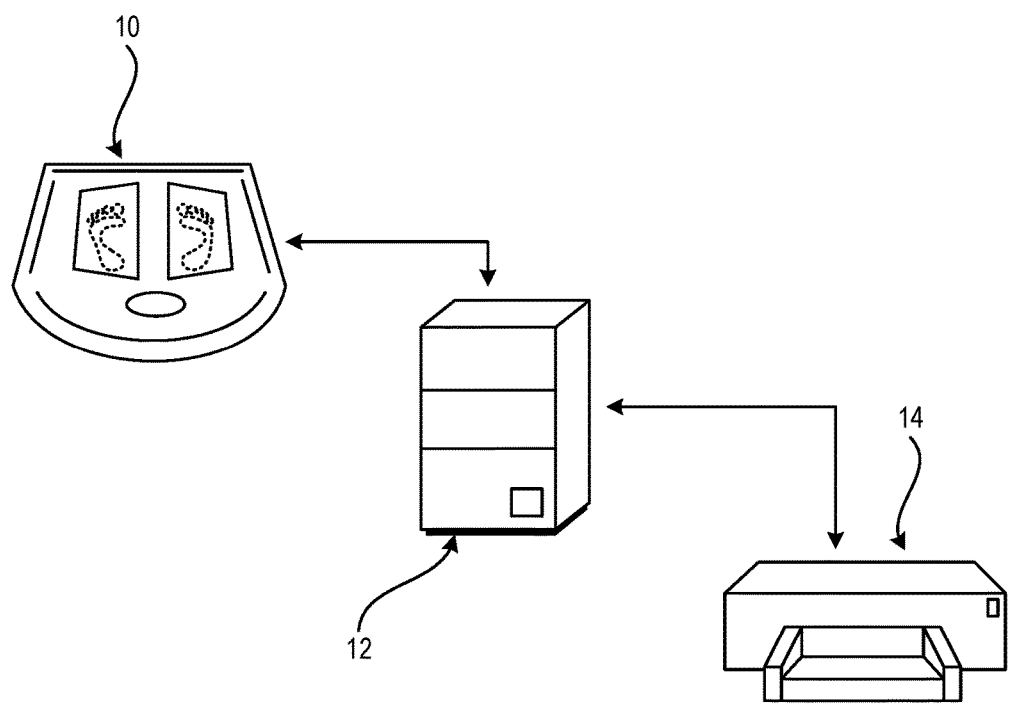
FIG. 1 is a basic block diagram of a system according to the present invention.

The concept underlying the invention is to manufacture a custom foot orthotic or insole through 3D printing based upon pressure measurements of an individual's foot. In a preferred embodiment the pressure measurements are mapped to create a data model of the foot after the individual stands upon an electronic pressure plate that uses pressure sensors and receives a pressure analysis of the foot. The data model is then input to the 3D printer to create a custom orthotic or insole that provides differing amounts of pressure unloading appropriate to the foot, by selectively locating individual compression cells within the orthotic or insole, with the specific compression cell used at a specific location being selected based on its pressure-unloading capability. Through material structure, material hardness, material softness, or a combination thereof, an orthotic or insole is produced that unloads and helps alleviate high pressure at various locations on the foot where indicated. The invention is not limited to the use of sensor devices to take pressure measurements. That is, any manner of obtaining pressure measurements, including but not limited to, thermal pressure measurement devices, or manual methods such as a Harris mat foot imprinter (e.g., methods where data is obtained and manually input to the system) can be used to obtain the pressure measurements and still fall within the scope of the claimed invention.

Polychromatic foot pressure data of the individual being scanned is collected by the foot scanner. Utilizing the pressure-point analysis readings from the electronic pressure plate measurements, readings from each sensor determine the hardness of various areas on the orthotic or insole. Softer areas of the orthotic or insole unload pressure in those spots to the harder areas of the orthotic or insole. The invention quantifies the varying and gradient foot pressures of the specific foot in issue by assigning and allocating numeric pressure values within a designated numeric range to each pressure reading (by way of example and not limitation, the range can be from 1 to 15 with 1 being lowest pressure and 15 being the highest pressure). Certain areas of the foot orthotic or insole can utilize either harder and/or softer materials to accommodate for various pressure readings of the individual's foot. The orthotic material can be softer in locations where foot pressure measurements read higher to help unload and alleviate excessive pressure and transfer pressure to other areas.

Alternatively (or in addition to varying the hardness or softness of the materials), certain areas of the foot orthotic or insole can utilize structural adjustments (e.g. the yielding capabilities, yielding parameters, weave process) to cause the structure to react differently to different pressures to accommodate for higher or lower pressure readings of an individual's foot.

The invention may utilize material softness, hardness, and/or material structure either individually or in any combination thereof to produce the orthotic or insole. Each pressure reading from the sensors is associated with a different structure, hardness, or combination thereof making the production of the orthotic or insole directly coordinated with the foot pressure analysis results. The invention converts the CAD (computer-aided design) model of an orthotic or insole into a grid which may vary in size (by way of example and not limitation, 1 cm×1 cm grid; ¼ cm×1 cm grid; etc.), where each individual grid file corresponds to a pressure sensor. From that matrix, an individual structure at a grid location, or a designated number of different groupings of structures, can be created based on the scan data in issue (by way of example and not limitation, there could be a single individual structure at a particular grid location, or 3 different groupings, 6 different groupings, 10 different groupings—the more groupings there are, the higher the "resolution" of the orthotic, and any number of groupings, smaller (including a single structure at a single grid location) or larger, can be utilized). Each point on the grid is assigned a pressure number and a structure, or grouping(s) of structures are placed at the grid locations accordingly. After assigning pressure map data to the individual models within the grid/matrix, the individual models are then identified by pressure number and the designated number (e.g., 6, 7, 8, . . . n) of consolidated models are created. The designated number of pressure models (e.g., 6) are then assigned specifically engineered scan strategies and internal support structures to create pressure response models of orthotics.

A preferred method of delivering usable foot pressure analysis data from the electronic pressure plates to the 3D printer is via stereolithography (STL) process. Stereolithographic models have been used in medicine since the 1990s, for creating accurate 3D models of various anatomical regions of a patient, based on datasets from computer scans. An exemplary conventional pressure plate device for use in practicing the present invention is the iStep® Pressure Plate, available from Aetrex Worldwide, Inc. of Teaneck, N.J. The iStep® system for use with this pressure plate is a digital pressure analysis system that accurately takes a pressure reading of a person's feet. The technology uses pressure sensors that are 0.25 $cm^2$, and properly identifies which areas of a person's feet absorb the most pressure and/or impact while standing.

When using the pressure plate, a person stands on the pressure plate for 10 to 30 seconds or some other suitable amount of time, and the sensors transmit signals to a computer to map out, and illustrate, the foot. The iStep® pressure plate has over 3700 sensors, but typically only about half end up in contact with the feet. In most cases, each foot encounters between 800-1200 sensors, and the technology gives a reading for each sensor based on the force that is placed on the sensor, forming a "pressure map" of the foot.

Similar to a fingerprint, this reading is individualized, and there are typically differences in pressure disbursement from one person to the next.

According to a preferred embodiment of the present invention a foot is scanned using pressure sensors and then the scan-data is processed using stereolithography and a processor configured to translate the data into input to a 3D printer that produces a custom orthotic or insole that reduces excessive foot pressure in areas where needed based upon an individual's pressure measurements, as described in more detail below. Systems and methods described for obtaining the foot pressure analysis data and its mapping to a particular foot are described in U.S. Pat. No. 7,493,230, incorporated fully herein by reference.

Under the preferred STL method, the file format will permit 3D shapes to be readable by 3D printer software and hardware. The transfer format may require programming adjustment and/or editing, including but not limited to manual adjustments and/or editing, depending upon the specific 3D printer in use and the printers' methods of communication between the software components in use; i.e., the 3D printer's application programming interface (API) that it provides and which may include its subroutine definitions, protocols, and other tools for adjusting and/or creating the application software.

Alternative formats of data transfer may be used including without limitation, manual data transfer.

FIG. 1 is a basic system diagram showing a system of the present invention. As can be seen if FIG. 1, a pressure sensor 10 for taking foot pressure measurements, such a as an electronic pressure plate sensor (e.g., an AETREX iStep NOVA foot scanner) is coupled to a processor 12 that is, according to the present invention, configured with code that will cause the processor to perform stereolithography on the data output from the pressure sensor 10, and output 3D printer data that will configure a 3D printer 14 to create a custom orthotic corresponding to the foot pressure measurements taken by the pressure sensor 10.

Figure 2:
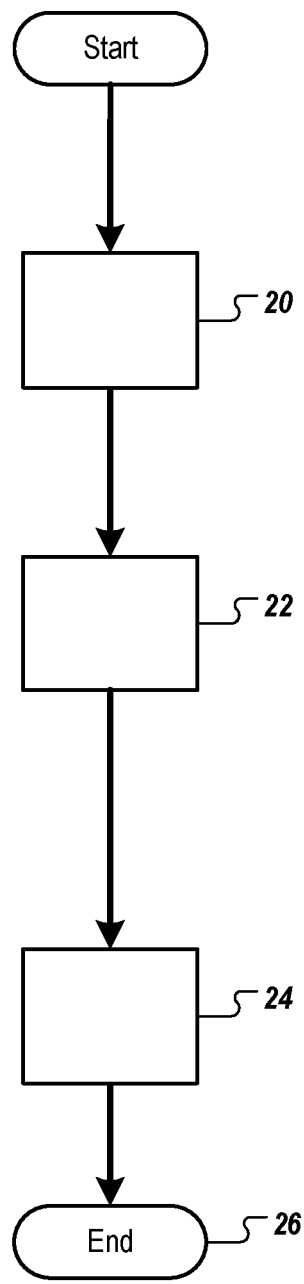
FIG. 2 is a flowchart showing the basic steps of the present invention.
Figure 3:
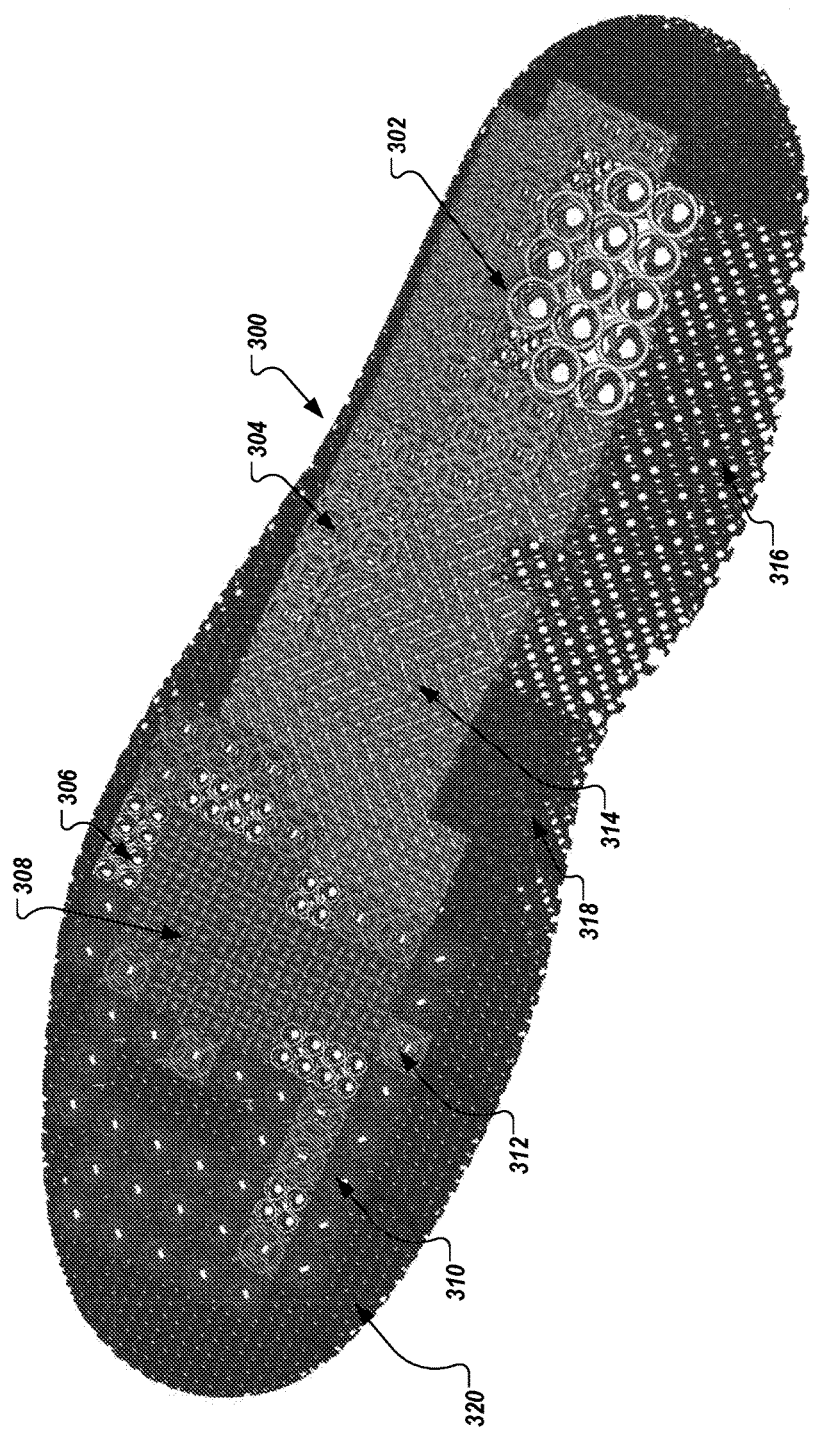
FIG. 3 illustrates a bottom view of an orthotic or insole insert created according to a method of the present invention.
Figure 4:
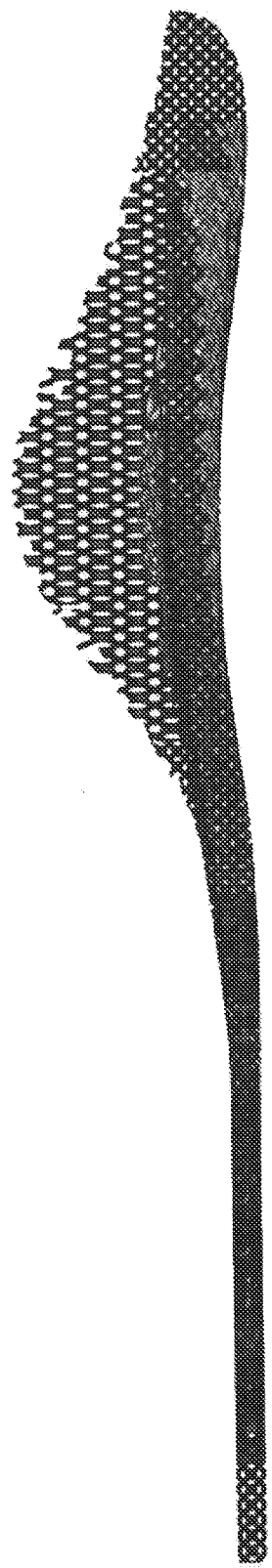
FIG. 4 illustrates a left view of an orthotic or insole insert created according to a method of the present invention.
Figure 5:
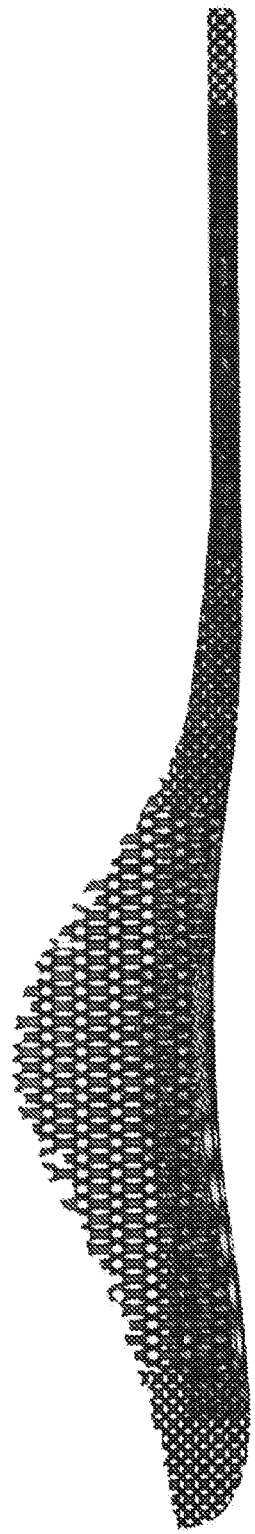
FIG. 5 illustrates a right view of an orthotic or insole insert created according to a method of the present invention.
Figure 6:
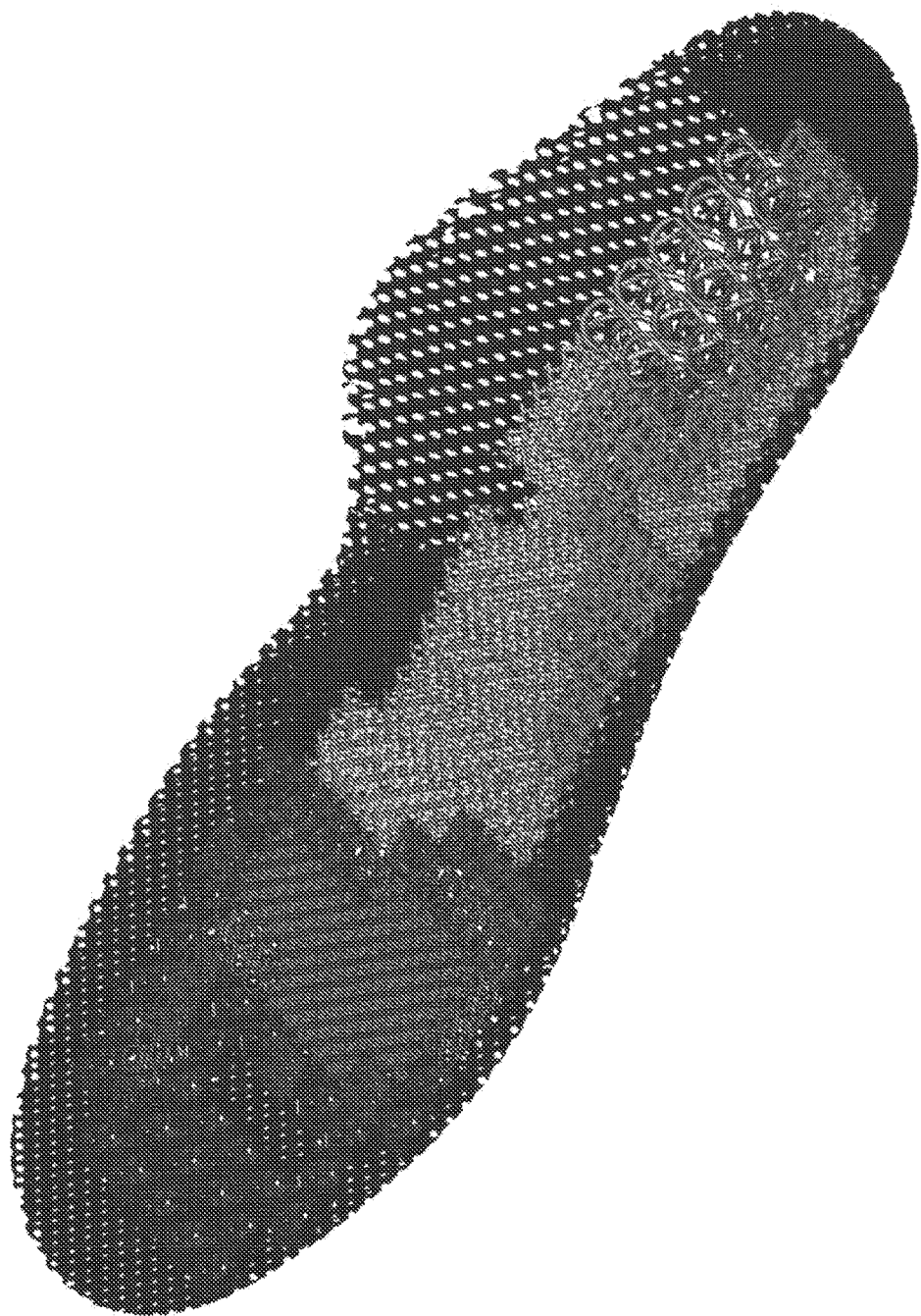
FIG. 6 illustrates a top perspective view of an orthotic or insole insert created according to a method of the present invention.

FIG. 2 is a flowchart describing the steps performed by the system of FIG. 1 to create the custom orthotic or insole. At step 20, a foot is placed on the pressure sensor and it takes pressure reading corresponding to the foot, and outputs the pressure data to the processor. At step 22 the processor receives the pressure data and uses a stereolithography process to transform the pressure data to 3D printer data that will instruct a 3D printer how to create the custom orthotic or insole. At step 24, the 3D printer data is received by the 3D printer, and creates a custom orthotic based on the 3D printer data. At Step 26 the process ends.

Referring now to FIGS. 3-20, an orthotic or insole and method of producing same according the present invention, are described. FIGS. 3-6 illustrate a bottom view, left view, right view, and top perspective view of an orthotic or insole insert created according to a method of the present invention. In FIG. 1, for example, it can be seen that the entire orthotic or insole insert is created of different types of compression cell structures 302, 304, 306, 308, 310, 312, 314, 316, 318, and 320. In accordance with the present invention, each compression cell type is created with a different structure, with each structure dictating the pressure response for each compression cell. For example, as discussed further below in more detail, compression cell type 302 utilizes larger, more flexible elements in its structure, making it more-easily compressed and thus giving it a greater pressure response and making it have a softer "feel" when placed underfoot. By way of contrast, compression cell type 310 utilizes a smaller, more solid and more compact structure, making it less-easily compressed and thus giving it a lesser pressure response and making it have a harder "feel" when placed underfoot. Each of the compression cell structures 302, 304, 306, 308, 310, 312, 314, 316, 318, and 320 differ in some manner such that, in this example, ten different pressure responses can be assigned to the various locations on the grid of the orthotic to enable very precise and high-resolution pressure response throughout the surface of the orthotic or insole. It is understood that these ten compression cell structures are provided for purpose of example only and that a person of ordinary skill in the art, given the information contained herein, could develop many other alternative compression cell structures that provide a particular desired pressure response, and all such alternatives and modifications fall within the scope of the invention claimed herein.

Figure 7:
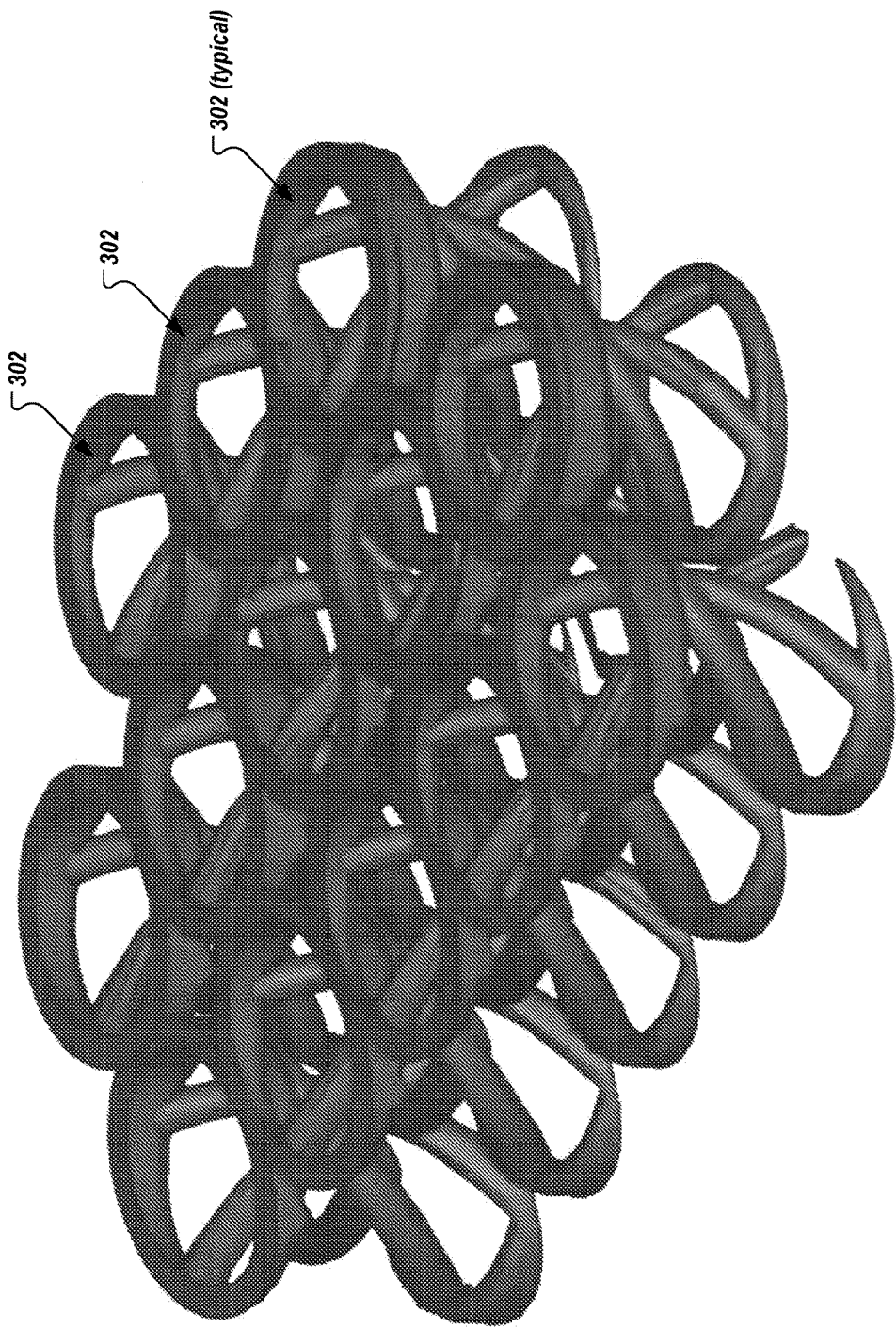
FIG. 7 illustrates the structure of compression cell in greater detail, where thirteen compression cells adjacent to each other, corresponding generally to the thirteen-cell configuration shown, for example, at the heel portion of FIG. 3.
Figure 8:
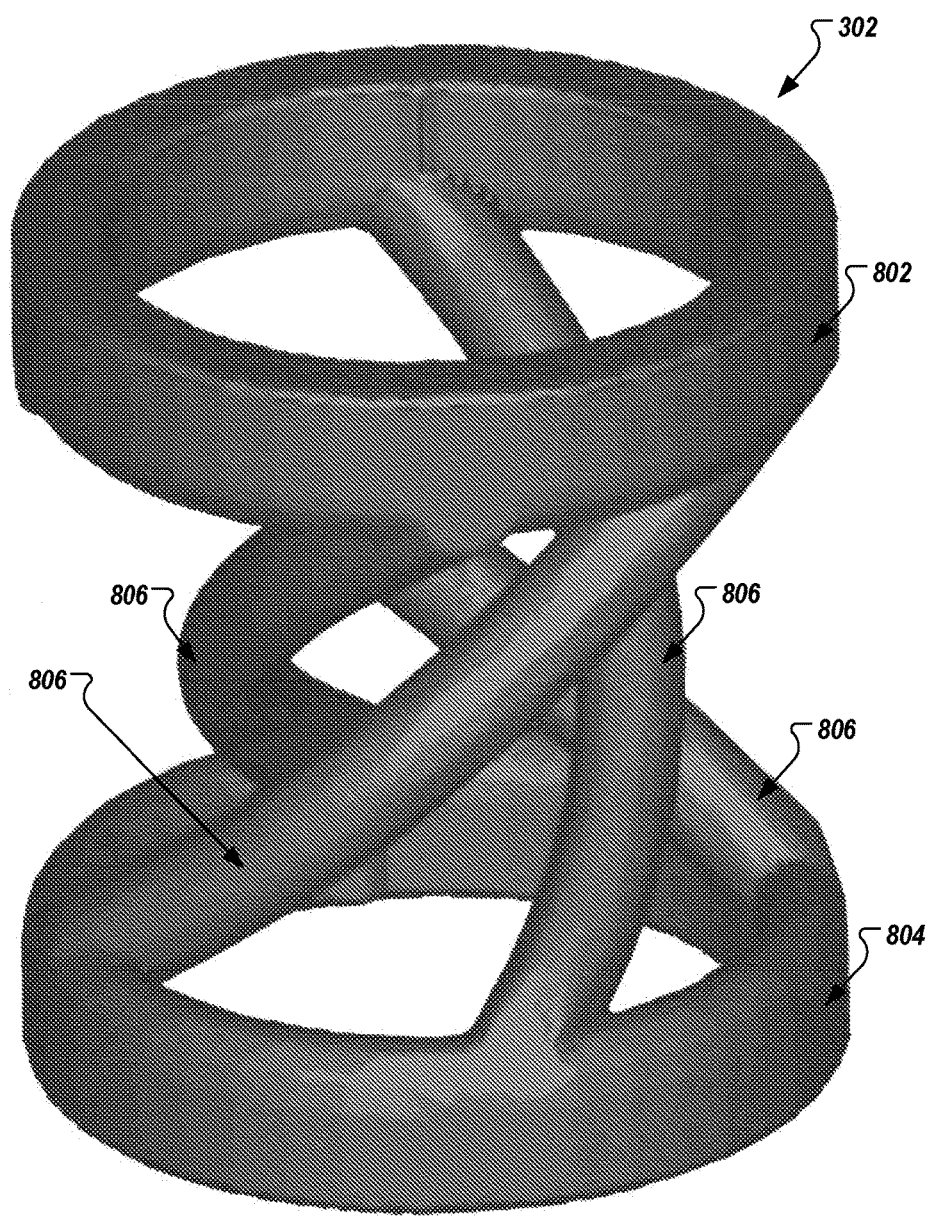
FIG. 8 illustrates a single compression cell.

FIGS. 7 and 8 illustrate the structure of compression cell 302 in greater detail. FIG. 7 illustrates thirteen compression cells 302 adjacent to each other, corresponding generally to the thirteen-cell configuration shown, for example, at the heel portion of FIG. 3. FIG. 8 illustrates a single compression cell 302. As can be seen in the Figures, each compression cell 302 comprises a generally circular top portion 802, a generally circular bottom portion 804, and, in this example, four generally helical or spiral flex elements 806 connecting circular top portion 802 and circular bottom portion 804, as shown. The material used to create compression cells 302 is, in a preferred embodiment, a resilient material that can flex, but will not break, when compressed. Examples of such material include (but are not limited to) TPU (thermoplastic polyurethanes), Nylon, and TPE (thermoplastic elastomers).

As can be understood from the above-description and the drawings, when force is applied downward onto top portion 802, the helical elements 806 deform in a downward direction, allowing top portion 802 to move downward, providing a "spongy" feel underfoot. Because the material is resilient, when downward the pressure on top portion 802 is reduced, the helical elements 806 bias back towards their at-rest position, thus also moving top portion 802 back upwards towards its at-rest position.

Figure 9:
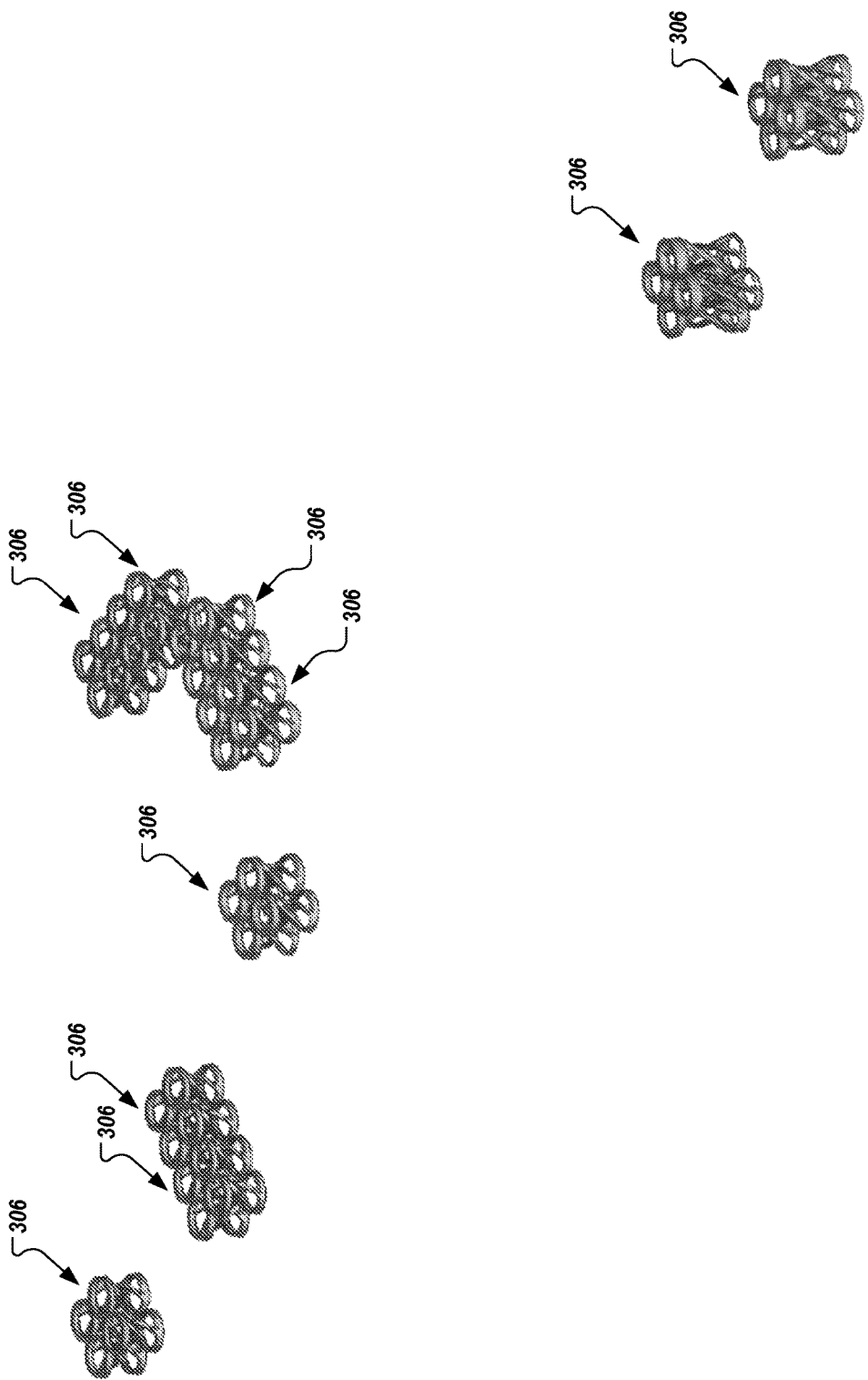
FIGS. 9 and 10 illustrate the structure of compression cell in greater detail.
Figure 10:
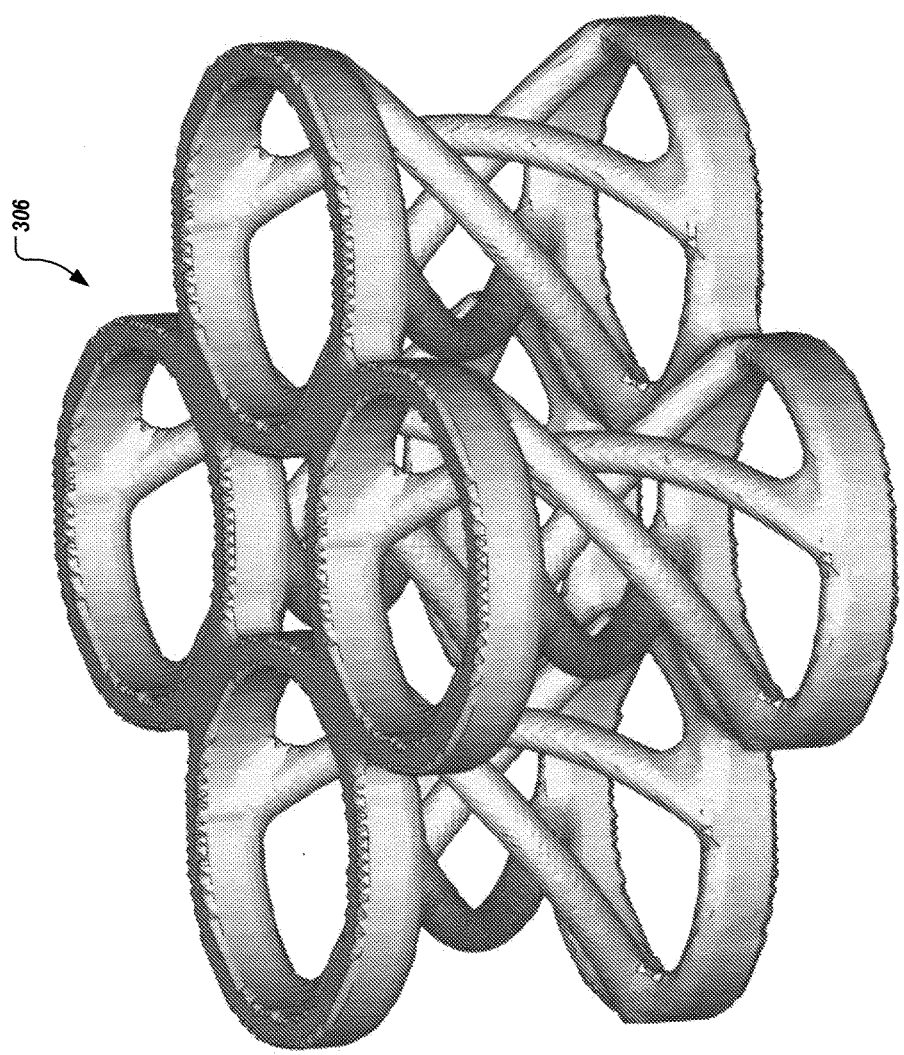

FIGS. 9 and 10 illustrate the structure of compression cell 306 in greater detail. As best shown in FIG. 9, each compression cell 306 comprises a grouping of four smaller versions of compression cell 302, joined together to form an essentially square cell, the details of which are best described in connection with FIG. 10. In this example, each compression cell 306 takes up approximately the same "footprint" as each compression cell 302; in other words, four smaller versions of compression cell 302 are joined together to form a single compression cell 306 which takes up essentially the same amount of space as compression cell 302. In a preferred embodiment the resilient material used for compression cell 302 is also used for compression cell 306 (and in fact, for all of the compression cells) so that, rather than having to use a different material with a different level of resilience, the pressure response is varied based on the structure used rather than the material used. This simplifies the 3D printing process, because there will be no need to vary the material used for the 3D printing.

It will be understood by one of ordinary skill in the art that by using, in compression cell 306, a greater amount of resilient material and a greater structural density than that of compression cell 302, compression cell 306 will be less-easily compressed and thus have a lesser pressure response than compression cell 302.

Figure 11:
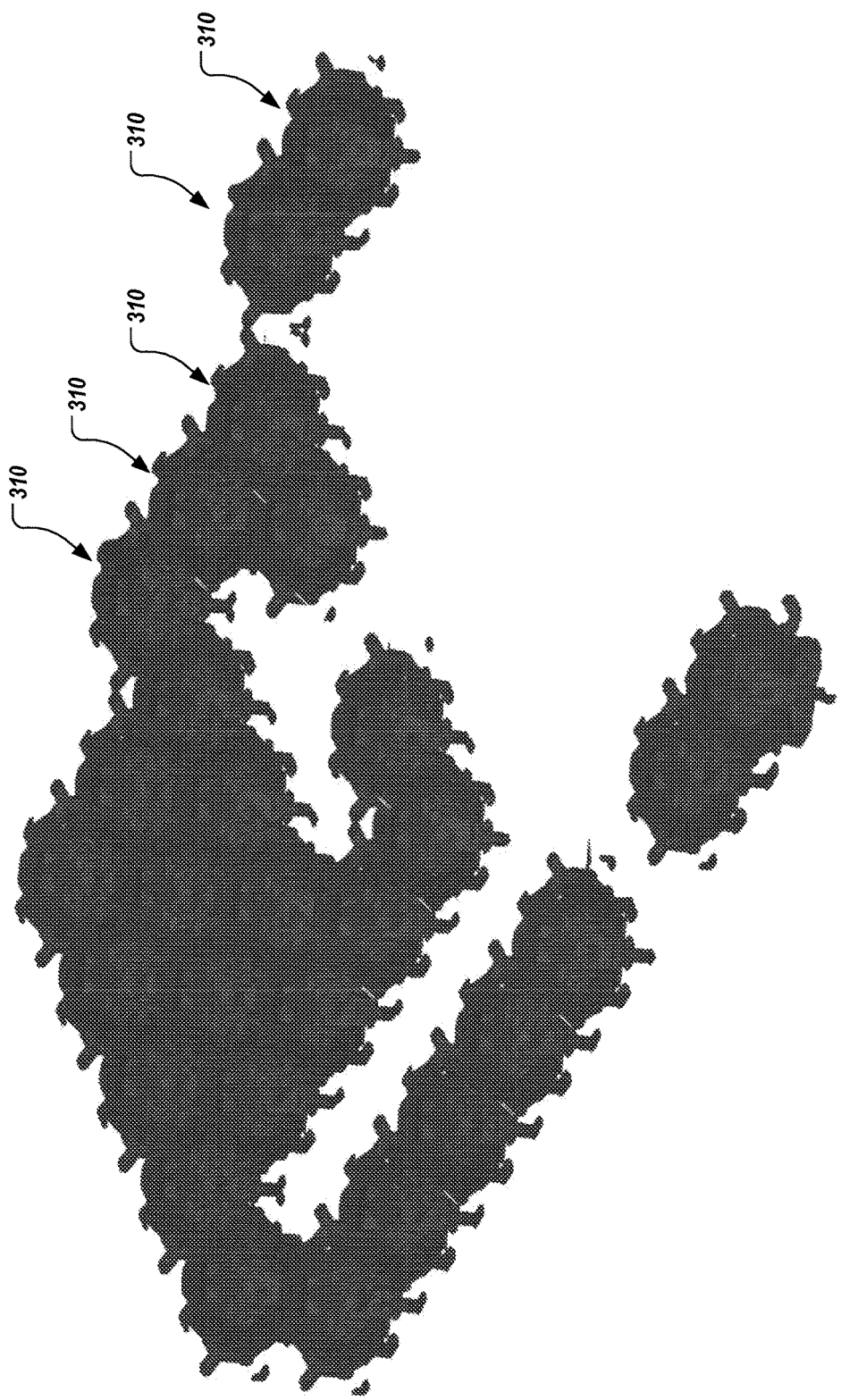
FIG. 11 illustrates twenty-nine individual compression cells.
Figure 12:
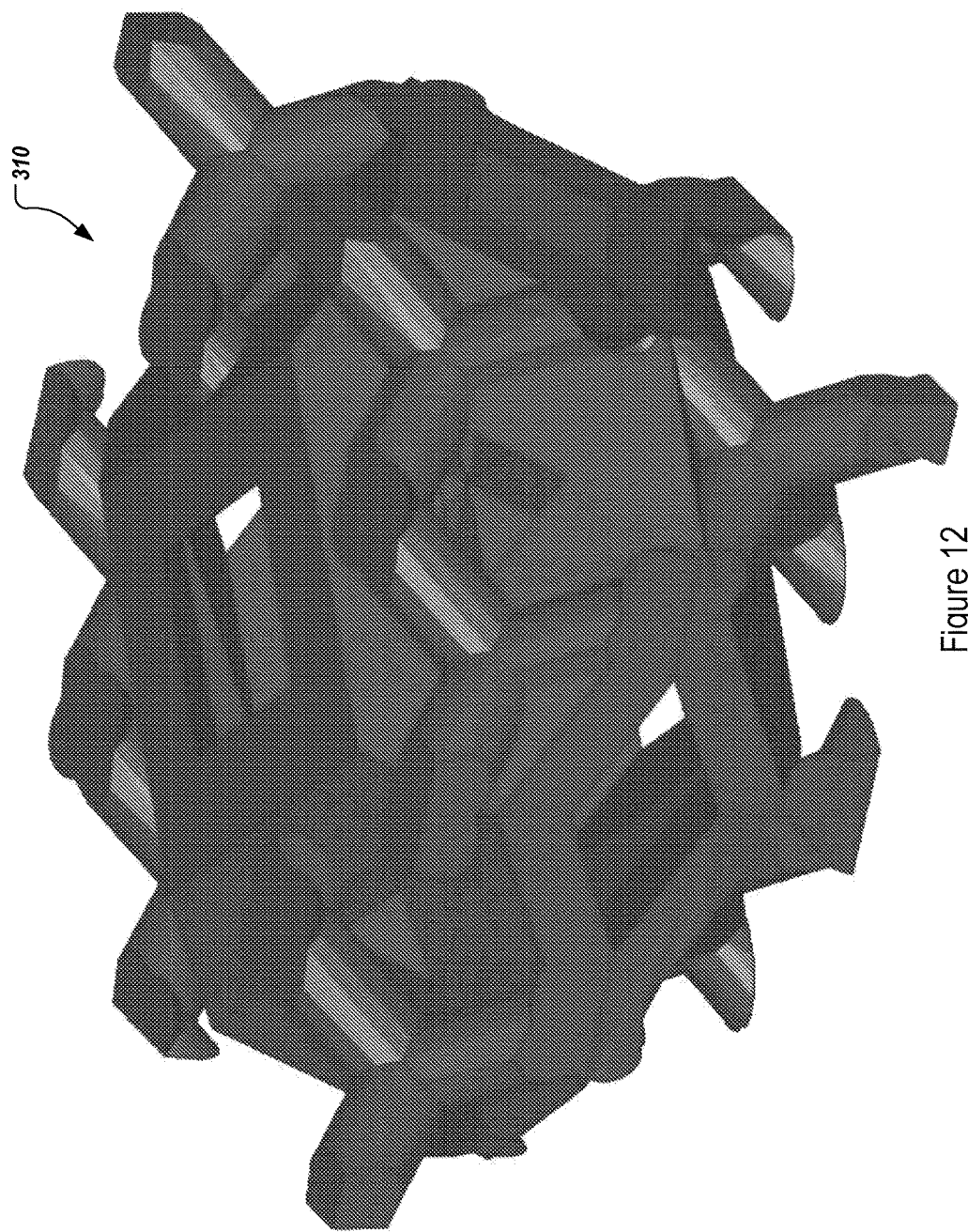
FIG. 12 illustrates a single compression cell.
Figure 13:
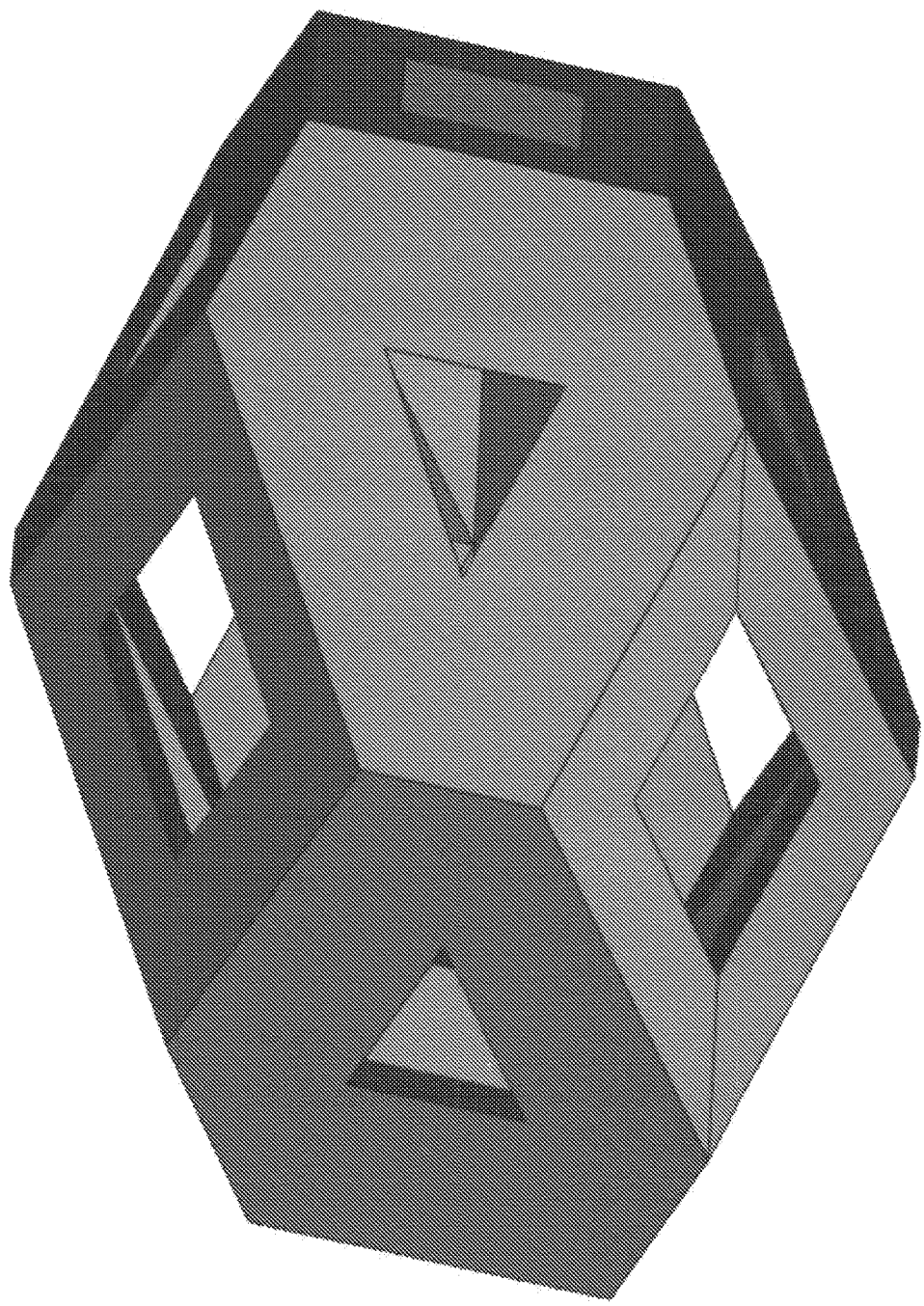
FIG. 13 illustrates an interior structure 1204 of the compression cell 310 shown in FIG. 12.
Figure 14:
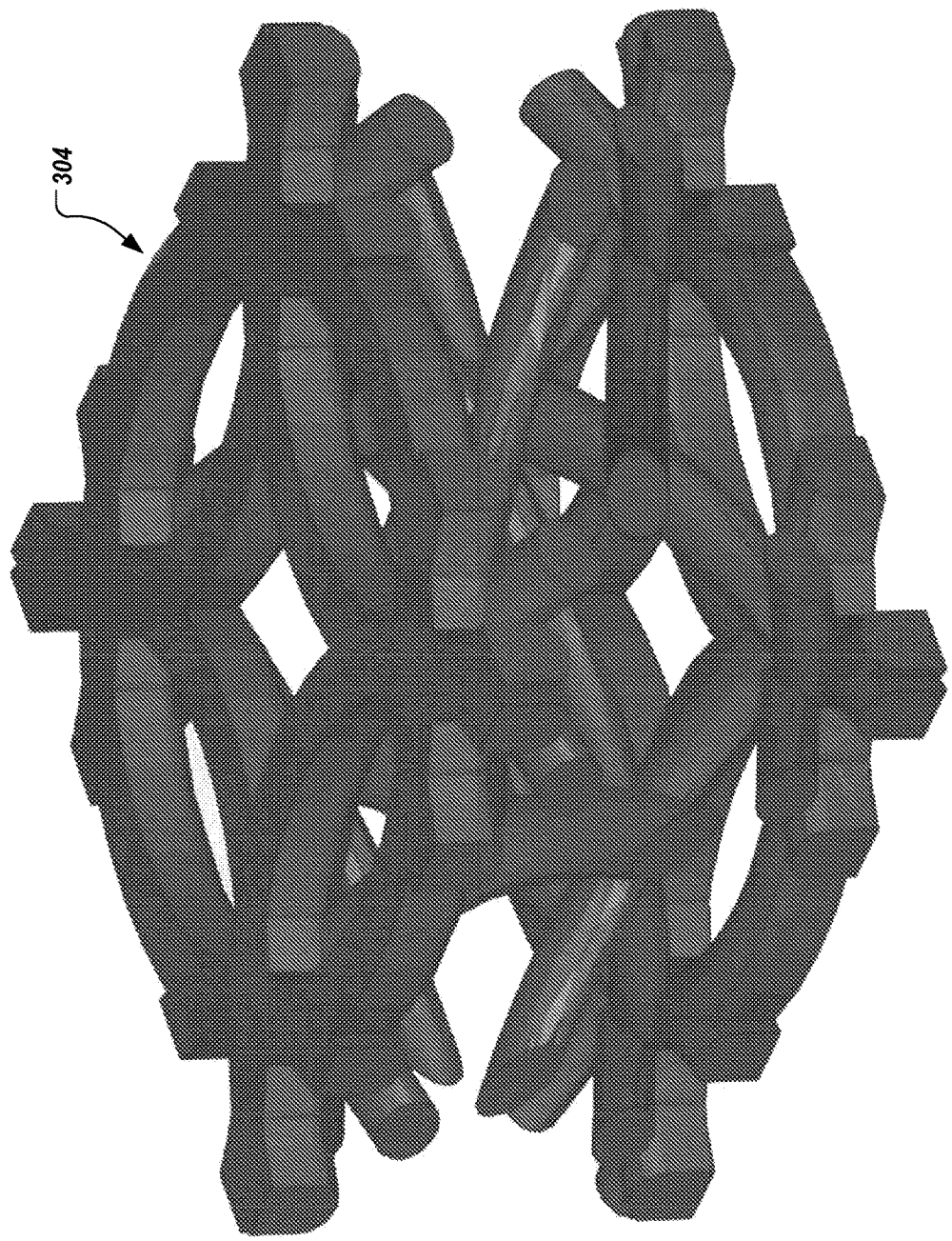
FIGS. 14 to 20 illustrate, without limitation, additional examples of configurations for compression cells that can be used and which are covered by the appended claims.
Figure 15:
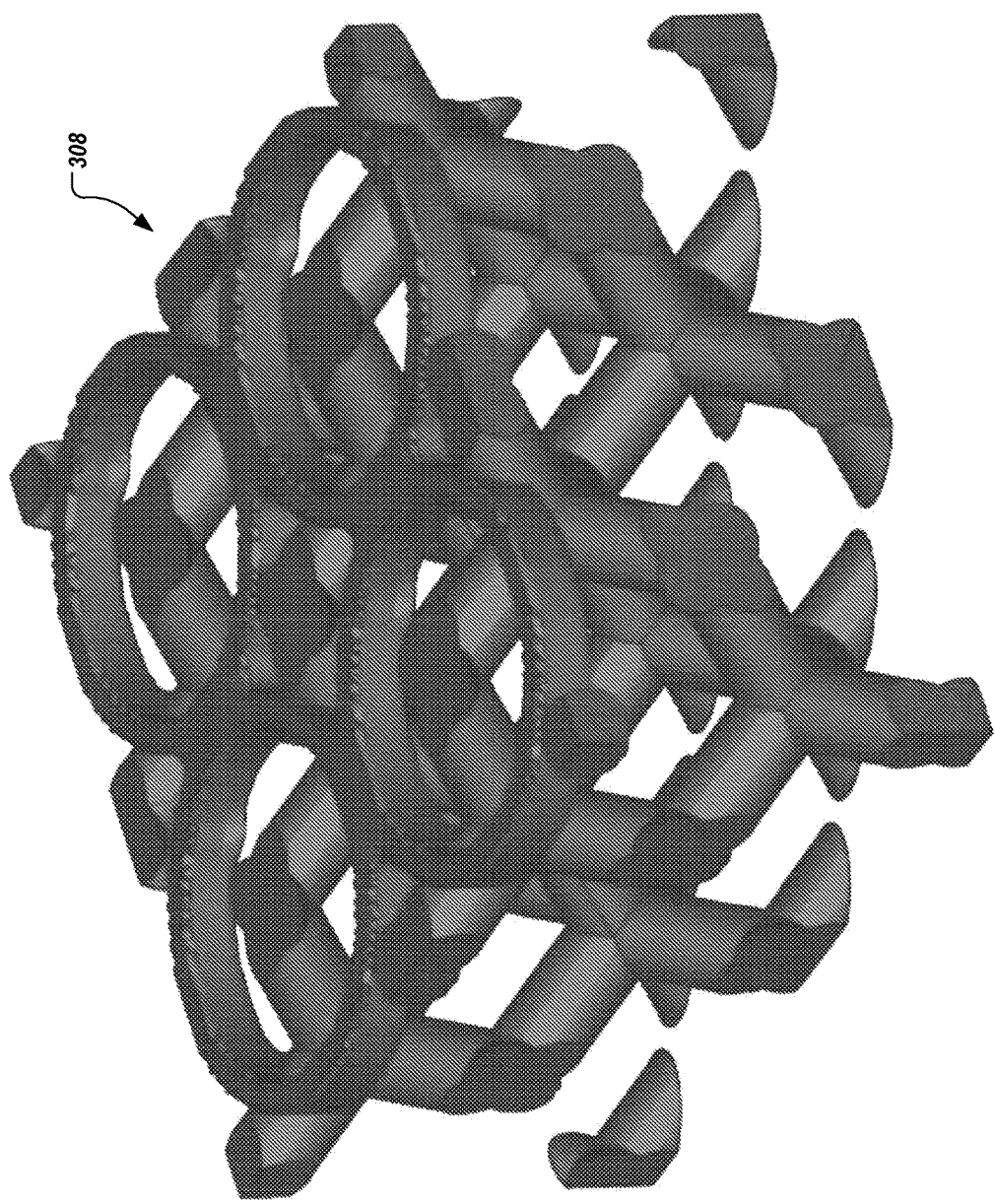
Figure 16:
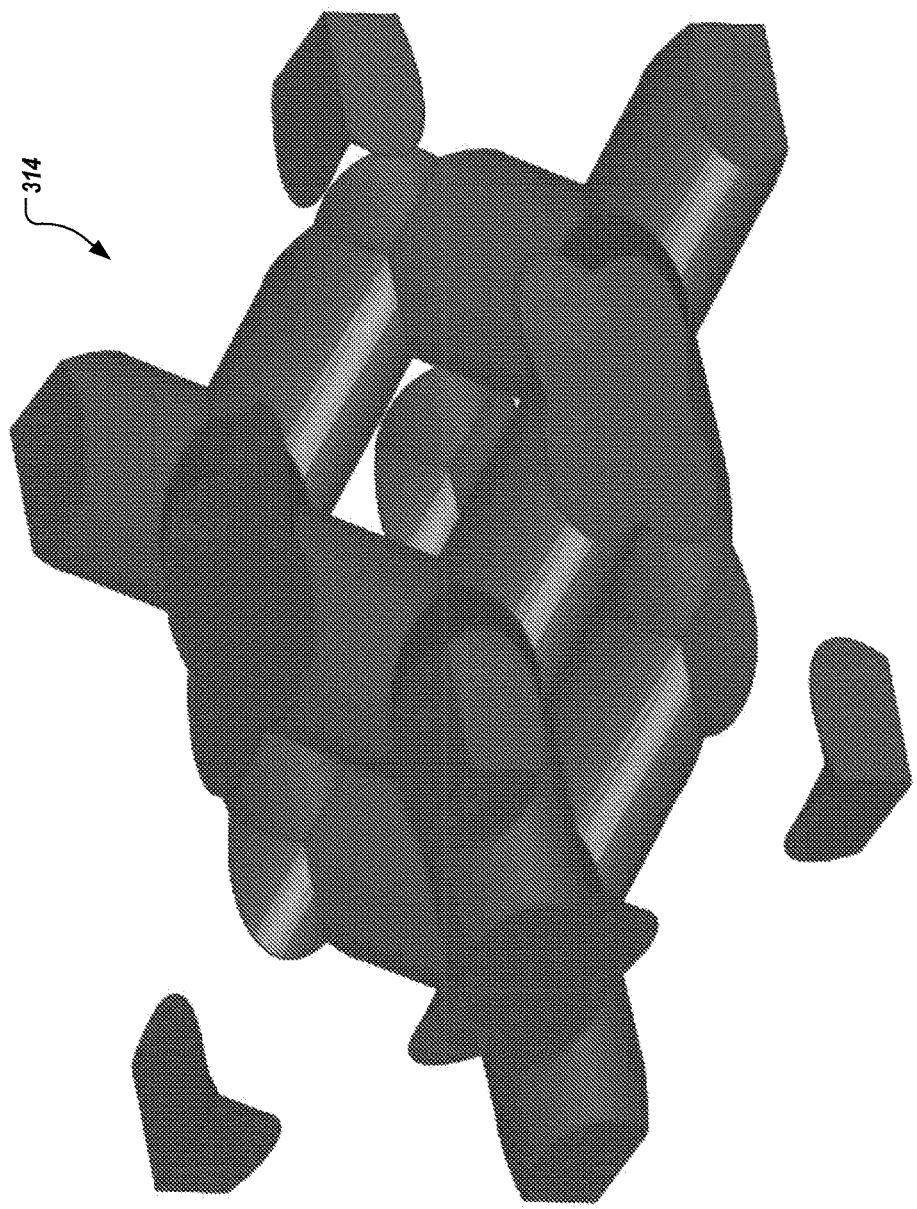
Figure 17:
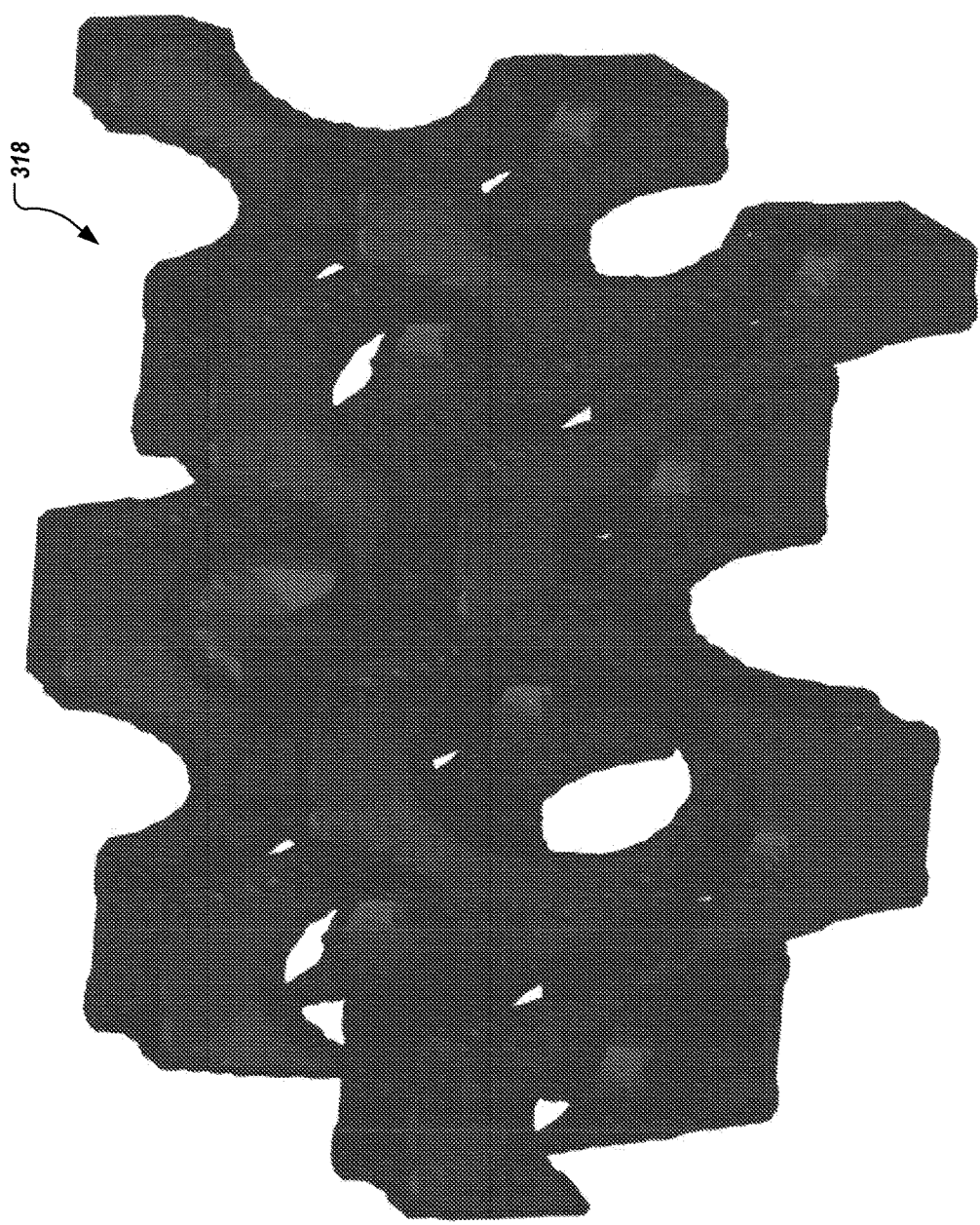
Figure 18:
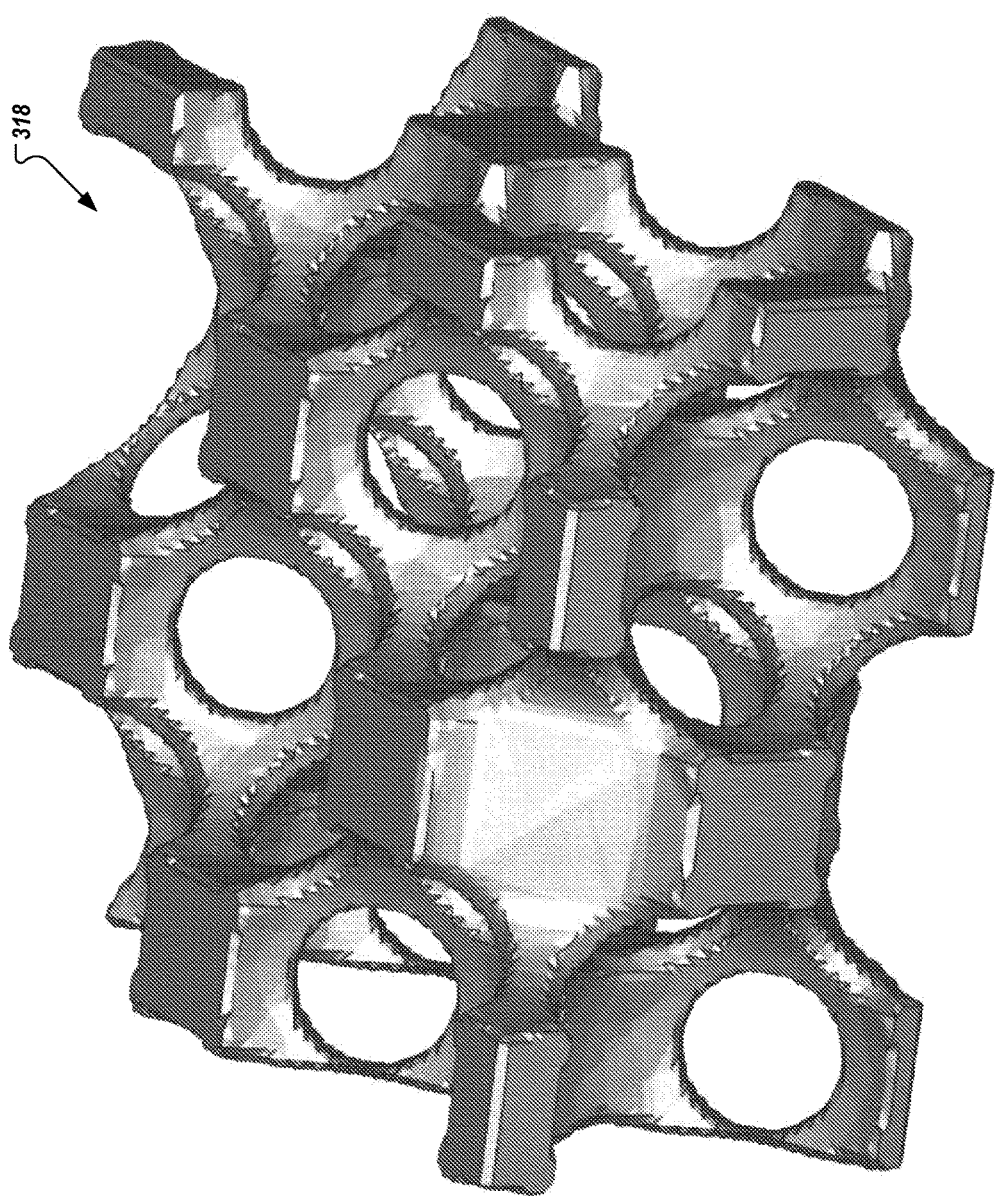
Figure 19:
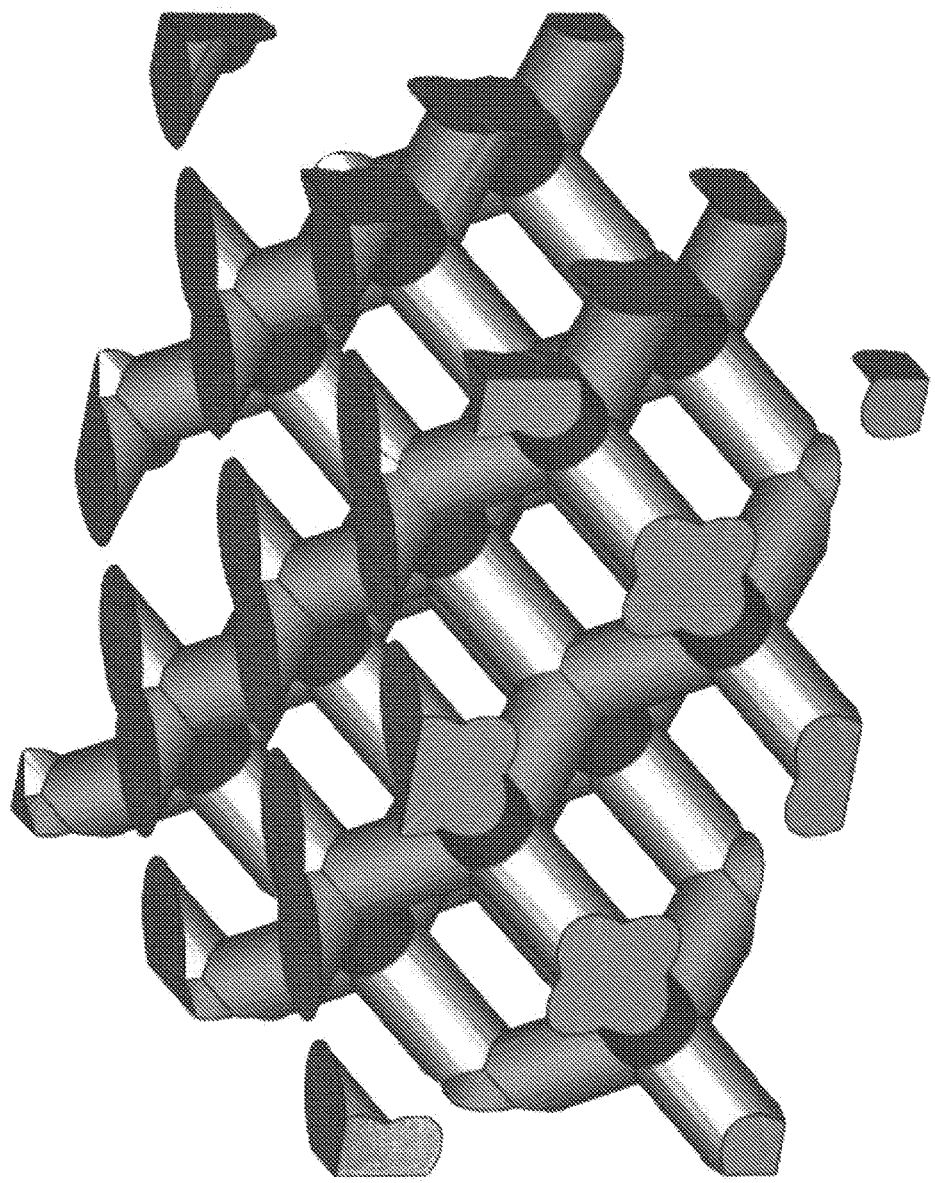
Figure 20:
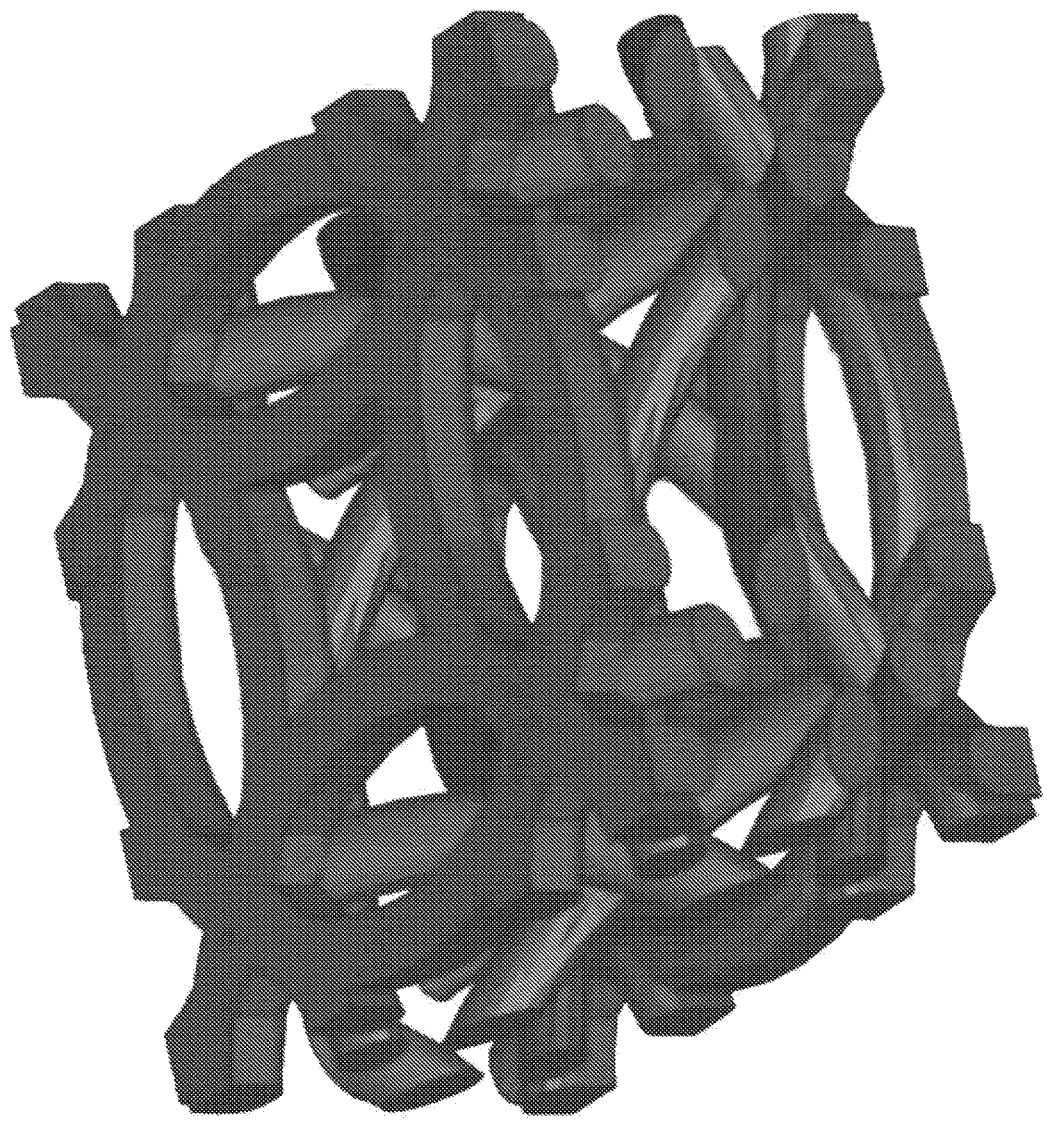

FIGS. 11-13 illustrate the structure of compression cell 310 in greater detail. FIG. 11 illustrates twenty-nine individual compression cells 310; FIG. 12 illustrates a single compression cell 310, and FIG. 13 illustrates an interior structure 1204 of the compression cell 310 shown in FIG. 12. As shown in FIG. 12, compression cell 310 comprises an external "web-like" structure 1202 connected to and surrounding a polyhedron-shaped interior structure 1204. As can best be seen in FIG. 13, polyhedron-shaped interior structure 1204 is a relatively dense structure that will take more downward pressure to compress than compression cells 302 or 306, and when coupled to and surrounded by the external web-like structure 1202 as shown in FIG. 12, is even less compressible. Compression cell 310 also takes up the same footprint as a single compression cell 302 or 306.

FIGS. 14-20 illustrate, without limitation, additional examples of configurations for compression cells that can be used and which are covered by the appended claims. As is known in the art, 3D printers can be supplied with instructions to create elements of virtually any shape that can be modeled and input to the printer; the compression cells described in detail above and shown in the drawing figures are provided as examples only and the claims herein are intended to cover not only the illustrated and described configurations, but compression cells of any configuration that can provide varying degrees of pressure response based on their structure and composition.

It is also understood that materials of different resilience can be used selectively throughout an orthotic, i.e., the materials need not be the same materials for each compression cell, although it provides for a simpler construction if the 3D printer uses a single material for all of the compression cells.

Any software steps described herein can be implemented using standard well-known programming techniques. The novelty of the above-described embodiment lies not in the specific programming techniques but in the use of the steps described and the various structures, materials, hardness/softness of materials, etc. disclosed to achieve the described results. Software programming code which embodies the present invention is typically stored in permanent storage. In a client/server environment, such software programming code may be stored with storage associated with a server. The software programming code may be embodied on any of a variety of known media for use with a data processing system, such as a USB drive, DVD, jump drive, or hard drive. The code may be distributed on such media, or may be distributed to users from the memory or storage of one computer system over a network of some type to other computer systems for use by users of such other systems. The techniques and methods for embodying software program code on physical media and/or distributing software code via networks are well known and will not be further discussed herein.

It will be understood that each element of the illustrations, and combinations of elements in the illustrations, can be implemented by general and/or special purpose hardware-based systems that perform the specified functions or steps, or by combinations of general and/or special-purpose hardware and computer instructions.

These program instructions may be provided to a processor to produce a machine, such that the instructions that execute on the processor create means for implementing the functions specified in the illustrations. The computer program instructions may be executed by a processor to cause a series of operational steps to be performed by the processor to produce a computer-implemented process such that the instructions that execute on the processor provide steps for implementing the functions specified in the illustrations. Accordingly, FIGS. 1-2 support combinations of means for performing the specified functions, combinations of steps for performing the specified functions, and program instruction means for performing the specified functions.

While there has been described herein the principles of the invention, it is to be understood by those skilled in the art that this description is made only by way of example and not as a limitation to the scope of the invention. Accordingly, it is intended by the appended claims, to cover all modifications of the invention which fall within the true spirit and scope of the invention.

The invention claimed is:

1. A method for 3D-printing an orthotic or insole, the method comprising:
   receiving pressure-point data or information of a foot using a pressure-analysis device;
   generating 3D printer input data or information for configuring a 3D printing device to print the orthotic or insole comprising a plurality of compression cells at particular locations of the orthotic or insole correlated to locations represented by the pressure-point data or information of the foot, each compression cell having a physical structure or material adapted to produce an underfoot pressure response based on a measured pressure at a corresponding location represented by the pressure-point data or information; and
   causing the 3D printing device to print the orthotic or insole based on the generated 3D printer input data or information.

2. The method of claim 1, wherein the locations of the orthotic or insole correlated to pressure-point data or information of the foot indicative of a higher pressure level are printed using softer material than the material used in the other locations of the orthotic or insole.

3. The method of claim 1, wherein the locations of the orthotic or insole correlated to pressure-point data or information of the foot indicative of a higher pressure level are printed using a structure that renders them softer underfoot than a structure used in the other locations of the orthotic or insole.

4. A method for custom making an orthotic or insole for footwear, the method comprising:
   receiving data or information obtained from a pressure detector, the data or information corresponding to a two-dimensional pressure map identifying pressure-point locations of the sole of a foot;
   determining a pressure number for each identified pressure-point location within the pressure map;
   creating, for each different pressure number, a compression cell corresponding to each different pressure number; and
   causing a 3D printing device to form the orthotic or insole by forming a plurality of compression cells each corresponding to the pressure number corresponding to each identified pressure-point location on the pressure map.

5. The method of claim 4, wherein the pressure number corresponding to a particular compression cell is determined by a physical structure used to form the particular compression cell.

6. The method of claim 4, wherein the pressure number corresponding to a particular compression cell is determined by a softness of material used to form the particular compression cell.

7. The method of claim 5, wherein the locations within the pressure map are defined by a grid having equally-sized grid locations.

8. The method of claim 7, wherein each compression cell is of the same size as each grid location.

9. The method of claim 7, wherein each compression cell is larger than the size of each grid location.

10. The method of claim 7, wherein each compression cell is smaller than the size of each grid location.

11. The method of claim 7, wherein multiple compression cells are combined to create a compression cell grouping.

12. The method of claim 11, wherein the orthotic or insole comprises multiple compression cell groupings.

13. The method of claim 12, wherein different compression cell groupings comprise a different physical structure.

14. A system for creating a custom orthotic or insole, the system comprising:

a foot pressure sensor configured to sense pressure-points of a foot placed thereon and to provide data or information corresponding to the sensed pressure-points;

a processor coupled to the foot pressure sensor and configured to receive the data or information corresponding to the sensed pressure-points and perform stereolithography on the data or information corresponding to the sensed pressure-points to generate 3D printer input data or information the 3D printer input data or information being descriptive of a plurality of compression cells each having a physical structure or material adapted to produce an underfoot pressure response based on a measured pressure at a corresponding location represented by the data or information corresponding to the sensed pressure-points; and a 3D printer coupled to the processor to receive the 3D printer input data or information and configured to form the to a custom orthotic or insole based on the 3D printer input data or information.

* * * * *